United States Patent [19]

McGinnis

[11] 4,298,023
[45] Nov. 3, 1981

[54] SPRING LOADED EXHALATION VALVE

[76] Inventor: Gerald E. McGinnis, 131 Kelvington Dr., Monroeville, Pa. 15146

[21] Appl. No.: 185,532

[22] Filed: Sep. 9, 1980

[51] Int. Cl.³ .............................................. F16K 15/06
[52] U.S. Cl. .................................... 137/529; 137/535; 137/542; 128/207.12; 128/206.15
[58] Field of Search ...................... 128/206.15, 207.12, 128/274, 205.24, 201.28; 137/542, 529, 535; 251/337

[56] References Cited

U.S. PATENT DOCUMENTS

| | | | |
|---|---|---|---|
| 1,359,631 | 11/1920 | Teed | 128/207.12 |
| 1,607,324 | 11/1926 | Voss | 137/535 |
| 2,406,888 | 9/1946 | Meidenbauer, Jr. | 128/205.24 |
| 2,547,882 | 4/1951 | Norton | 137/535 |

FOREIGN PATENT DOCUMENTS

| | | | |
|---|---|---|---|
| 545595 | 9/1957 | Canada | 137/535 |
| 60787 | 2/1891 | Fed. Rep. of Germany | 137/529 |
| 444962 | 5/1936 | United Kingdom | 128/207.12 |

Primary Examiner—Henry J. Recla
Attorney, Agent, or Firm—Brown, Flick & Peckham

[57] ABSTRACT

An exhalation valve for inhalation therapy includes a base member provided with an exhalation port encircled by a valve seat for a valve closure disc, the center of which is connected to the inner end of a pin extending outwardly away from the disc and slidably mounted in a sleeve spaced from the disc. The sleeve is held rigidly by a support connected with the base member. A number of Constant-Force Compression coil springs extend between the sleeve and disc and are bowed outwardly away from the pin. The ends of the springs are connected with the sleeve and closure disc to urge the disc toward the valve seat. The springs exert a substantially constant pressure against the disc as it is moved outwardly away from the valve seat by air flowing out through the valve port.

6 Claims, 4 Drawing Figures

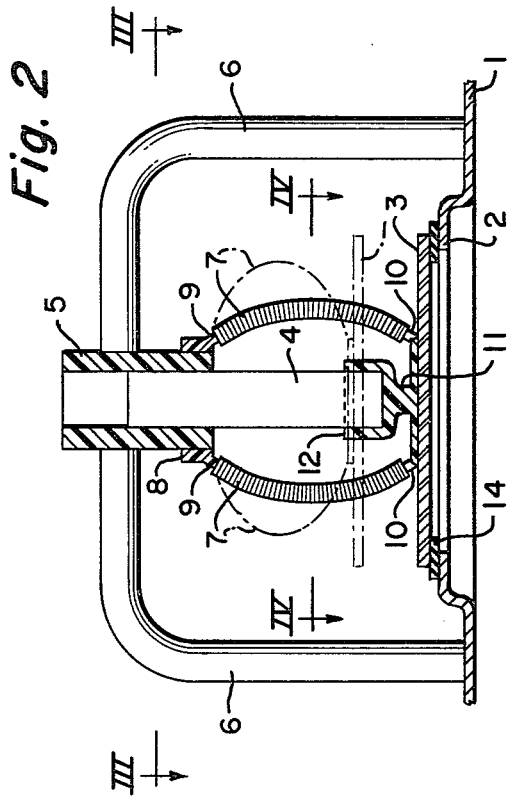
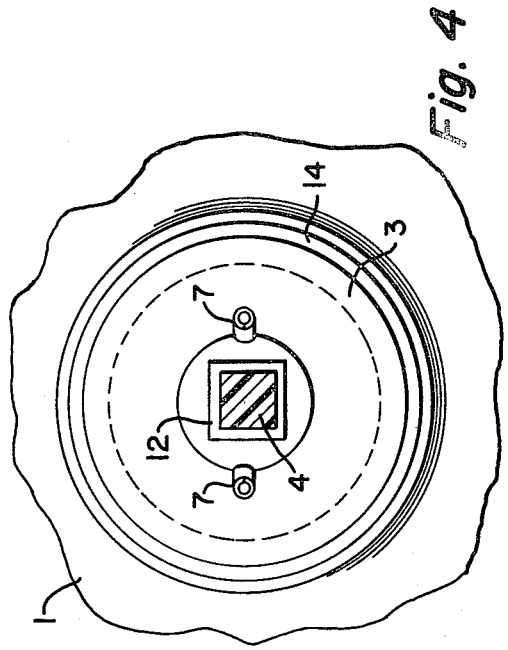
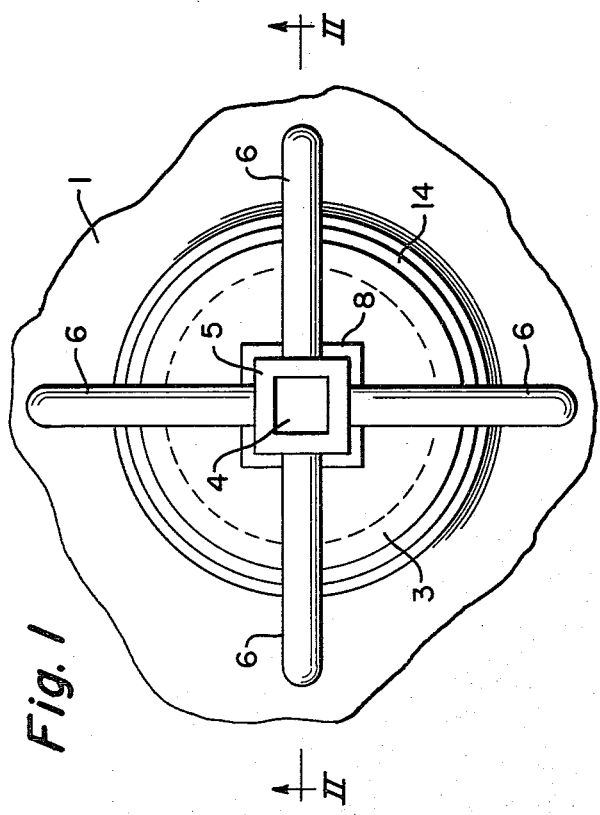
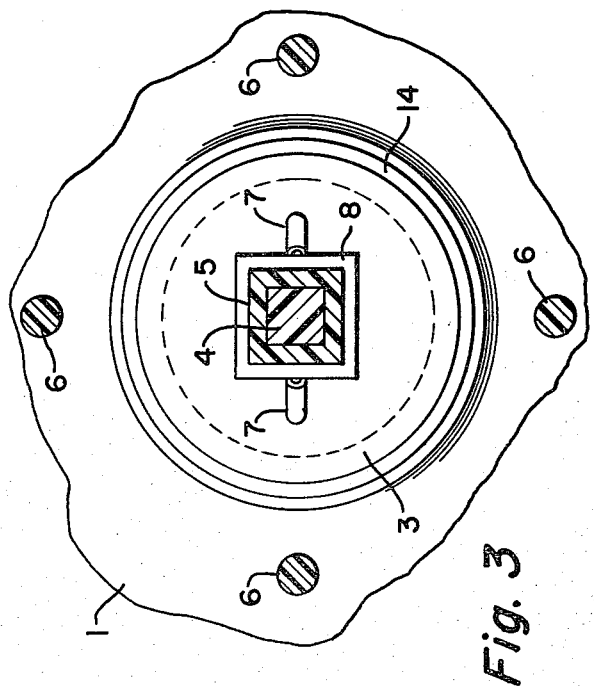

SPRING LOADED EXHALATION VALVE

In recent years a therapeutic technique has been developed to prevent lung problems in patients with upper abdominal or thoracic surgery. This treatment is given to keep a patient's lungs under positive air pressure during the exhalation phase. The equipment used may consist of commonly available respiratory devices that will provide gas flow of air or oxygen-enriched air, with or without added humidity, to the patient through a tube connected to an endotracheal tube, a face mask or mouthpiece. There is a high rate of flow to the patient which can either be inhaled or which will escape through an exhalation valve. During inhalation, the air pressure will remain constant as long as the flow rate through the tube exceeds the maximum flow rate that the patient requires instantaneously during inhalation. During exhalation, the incoming gas flow and the gas exhaled by the patient pass out through the exhalation valve. The optimum valve for such treatment should have characteristics such that from zero flow through flow rates of approximately 100 liters a minute or higher the airway pressure should be constant. If the valve does not have such constant pressure characteristics, the patient will experience increasing resistance as the flow rate increases. This will result in higher work of breathing and discomfort for the patient and possible negation of the beneficial effects of the treatment. The problem, technically, of making an exhalation valve with suitably flat characteristics results primarily from a typical low pressure of 6 to 10 centimeters of water pressure exerted by the valve. When springs are used for these low forces, the springs tend to be fragile, hard to support and have unstable operating characteristics at higher gas flows.

It is among the objects of this invention to provide an exhalation valve, using springs for doing it, which will maintain low airway pressure substantially constant over a wide flow rate range.

The preferred embodiment of the invention is illustrated in the accompanying drawings, in which FIG. 1 is a plan view;

FIG. 2 is a vertical section taken on the line II—II of FIG. 1;

FIG. 3 is a horizontal section taken on the line III—III of FIG. 2; and

FIG. 4 is a horizontal section taken on the line IV—IV of FIG. 2.

Referring to the drawings, a base member 1 is provided with an exhalation port encircled by a valve seat 2. The base member may be either a face mask, or a separate valve housing connected to the end of the exhalation tube that is connected to the mask, mouthpiece or endotracheal tube. There is a valve closure disc 3 for this port. The center of the disc is connected to the inner end of a pin 4 extending outwardly away from the disc. The pin is slidably mounted in a sleeve 5 spaced from the disc and rigidly supported in any suitable manner, such as by a bracket 6, from the base member. The pin and sleeve are noncircular in cross section so that the pin cannot turn in the sleeve.

Connected to the sleeve and the closure disc are two or more coil springs 7 that are bowed outwardly away from the pin while the valve is closed, and that are bowed more sharply as the disc leaves the valve seat during opening of the valve, as indicated in dotted lines in FIG. 2. To provide highly desirable friction-free operation of the springs with an absence of torque on their ends, the connection of the springs to the sleeve and disc should permit the ends of the springs to turn as the bowing of the springs is increased. One way of doing this is to mount or form a collar 8 on the inner end of the sleeve and to provide the collar with diverging flexible prongs 9 that project into the ends of the springs. The collar and prongs may be a molded soft plastic and integrally connected to one another. Similar prongs 10, extending into the other end of the springs, may project from a plastic member cemented to the center of the disc. This member has a central projection 11 terminating in a cup 12, in which the inner end of pin 4 is rigidly mounted. The projection 11 is flexible so that the disc can seat properly on the valve seat even if the pin is not exactly perpendicular to the disc.

Springs 7 are constant-force compression springs, in which the coil of spring wire is provided with a large initial axial tension between adjacent turns. As the spring is flexed to bow it, the turns separate along the convex side of the bow and are pressed more tightly together along the concave side of the bow. Such a spring is disclosed in U.S. Pat. No. Re. 23,974, entitled Constant Compression Springs. These previously patented springs are sold by the Hunter Spring Division of Ametek, Inc. under the trademark Flex'ator. When these springs are bowed, the resulting torque that tends to straighten them provides a substantially constant force throughout a convenient range of motion.

By the use of the bowed Constant-Force Compression Springs, they do not exert increasing resistance to movement of the valve disc farther away from its seat as the air flow rate out through the valve increases, so no greater effort by the patient is required in order to exhale when the flow rate is relatively great than when relatively small.

Since the closing force exerted by the springs is very low, typically 20 to 30 grams for a practical size valve port used in inhalation therapy, there is no excess force to assure flat seating of the closure disc on its seat or to overcome frictional effects. Consequently, to assure proper seating of the disc, an annular membrane seal 14 between the valve seat and disc is secured to the seat. This seal projects inwardly from the valve seat a short distance to overlie the marginal area of the valve port. A slight air pressure against the projecting area of the seal will hold it against the closure disc and thereby seal the valve even if the disc does not seat flat against the annular seal.

The force exerted by the constant-force compression springs depends upon their diameter, the number used and, for a given diameter, the length of the springs.

According to the provisions of the patent statutes, I have explained the principle of my invention and have illustrated and described what I now consider to represent its best embodiment. However, I desire to have it understood that, within the scope of the appended claims, the invention may be practiced otherwise than as specifically illustrated and described.

I claim:

1. An exhalation valve for inhalation therapy, comprising a base member provided with an exhalation port encircled by a valve seat, a valve closure disc for said port, a pin connected to the center of said disc and extending outwardly away from the side of the disc remote from the port, a sleeve spaced from said disc and slidably receiving said pin, a support connecting the sleeve to said base member, at least two constant-force compression coil springs extending between said sleeve and disc, and means on said sleeve and disc for connecting the ends of the springs thereto, said springs being bowed outwardly away from said pin when said disc is seated on said valve seat and urging said disc toward the valve seat to close the valve, the springs exerting a substantially constant pressure against the disc as it is moved outwardly away from the valve seat by air flowing out through said port.

2. An exhalation valve according to claim 1, in which said connecting means are flexible prongs projecting into the ends of said coil springs.

3. An exhalation valve according to claim 1, including flexible means connecting the inner end of said pin with said closure disc.

4. An exhalation valve according to claim 3, in which said flexible means carries flexible prongs projecting into the adjacent ends of said coil springs, and said sleeve carries flexible prongs projecting into the other end of the springs.

5. An exhalation valve according to claim 1, in which said pin and sleeve are noncircular in cross section to prevent the pin from turning in the sleeve.

6. An exhalation valve according to claim 1, including an annular membrane secured to said valve seat between it and said closure disc and projecting inwardly beyond the seat.

* * * * *